(12) United States Patent
Miura (10) Patent No.: US 11,124,194 B2
(45) Date of Patent: Sep. 21, 2021

(54) WAKEFULNESS INDUCING SYSTEM (71) Applicant: Marelli Corporation, Saitama (JP)

(72) Inventor: Hiromasa Miura, Saitama (JP)

(73) Assignee: Marelli Corporation, Saitama (JP)

( * ) Notice: Subject to any disclaimer, the term of this patent is extended or adjusted under 35 U.S.C. 154(b) by 67 days.

(21) Appl. No.: 16/650,364

(22) PCT Filed: Jun. 19, 2018

(86) PCT No.: PCT/JP2018/023348
§ 371 (c)(1),
(2) Date: Mar. 24, 2020

(87) PCT Pub. No.: WO2019/064736
PCT Pub. Date: Apr. 4, 2019

(65) Prior Publication Data
US 2020/0231165 A1   Jul. 23, 2020

(30) Foreign Application Priority Data
Sep. 27, 2017   (JP) .............................. JP2017-186838

(51) Int. Cl.
*B60W 40/08* (2012.01)
*B60W 60/00* (2020.01)
*B60H 1/00* (2006.01)

(52) U.S. Cl.
CPC ......... *B60W 40/08* (2013.01); *B60H 1/00271* (2013.01); *B60W 60/0051* (2020.02);
(Continued)

(58) Field of Classification Search
CPC .......................... B60W 40/08; B60W 60/0051
See application file for complete search history.

(56) References Cited

U.S. PATENT DOCUMENTS 9,725,036 B1*   8/2017  Tarte ..................... B60K 28/066
2017/0334263 A1* 11/2017  Schumacher ............ B60N 2/56
(Continued)

FOREIGN PATENT DOCUMENTS

| JP | 2011-118831 A | 6/2011 |
| JP | 2011-159108 A | 8/2011 |

(Continued)

OTHER PUBLICATIONS

International Preliminary Report on Patentability dated Apr. 2, 2020 of International Application No. PCT/JP2018/023348.

*Primary Examiner* — Jess Whittington
(74) *Attorney, Agent, or Firm* — Young Basile Hanlon & MacFarlane, P.C.

(57) ABSTRACT

A wakefulness inducing system is capable of appropriately inducing a wakeful state in a driver even in a self-driving vehicle. A wakefulness inducing system includes a wakefulness degree sensing apparatus that senses the degree of wakefulness of a driver, a touch operation apparatus including a touch operation interface that detects contact by the operating hand of the driver, and a self-driving apparatus that controls self-driving of a vehicle. When the wakefulness degree sensing apparatus senses a reduction in the degree of wakefulness of the driver, the self-driving apparatus provides an instruction to the driver to move the operating hand to the touch operation interface, and the temperature of the operating hand is lowered in the touch operation interface upon detection of contact of the operating hand by the touch operation interface.

7 Claims, 5 Drawing Sheets

(52) U.S. Cl.
CPC .............. *B60H 2001/003* (2013.01); *B60W 2040/0827* (2013.01)

(56) References Cited

U.S. PATENT DOCUMENTS

2017/0364070 A1   12/2017  Oba
2019/0004513 A1    1/2019  Chiba et al.

FOREIGN PATENT DOCUMENTS

| | | |
|---|---|---|
| JP | 2013-015993 A | 1/2013 |
| JP | 2016-115356 A | 6/2016 |
| JP | 2017-027180 A | 2/2017 |
| JP | 2017-030518 A | 2/2017 |

\* cited by examiner

WAKEFULNESS INDUCING SYSTEM

CROSS-REFERENCE TO RELATED APPLICATION

The present application claims priority to and the benefit of Japanese Patent Application No. 2017-186838 filed Sep. 27, 2017, the entire contents of which are incorporated herein by reference.

TECHNICAL FIELD

The present disclosure relates to a wakefulness inducing system.

BACKGROUND

A technique for controlling a reduction in the degree of wakefulness of a driver of a vehicle and appropriately inducing a wakeful state is known. For example, upon sensing a reduction in the degree of wakefulness of a driver, the driving support apparatus disclosed in patent literature JP2013-015993A blows cool air on the driver's hands holding the steering wheel.

SUMMARY

In a self-driving vehicle that does not require the steering wheel to be held, the driver's hands may be in various positions during self-driving. In this case, the driving support apparatus disclosed in JP2013-015993A cannot blow cool air onto hands on the steering wheel and therefore cannot obtain the effect of rousing the driver.

The present disclosure was conceived from this perspective and aims to provide a wakefulness inducing system capable of appropriately inducing a wakeful state in a driver even in a self-driving vehicle.

To solve the aforementioned problem, a wakefulness inducing system according to an embodiment of the present disclosure includes:

a wakefulness degree sensing apparatus configured to sense a degree of wakefulness of a driver;

a touch operation apparatus comprising a touch operation interface configured to detect contact by an operating hand of the driver; and a self-driving apparatus configured to control self-driving of a vehicle;

such that when the wakefulness degree sensing apparatus senses a reduction in the degree of wakefulness of the driver, the self-driving apparatus provides an instruction to the driver to move the operating hand to the touch operation interface, and a temperature of the operating hand is lowered in the touch operation interface upon detection of contact of the operating hand by the touch operation interface.

A wakefulness inducing system according to an embodiment of the present disclosure is capable of appropriately inducing a wakeful state in a driver even in a self-driving vehicle.

DETAILED DESCRIPTION

Embodiments of the present disclosure are described below with reference to the drawings.

Figure 1:
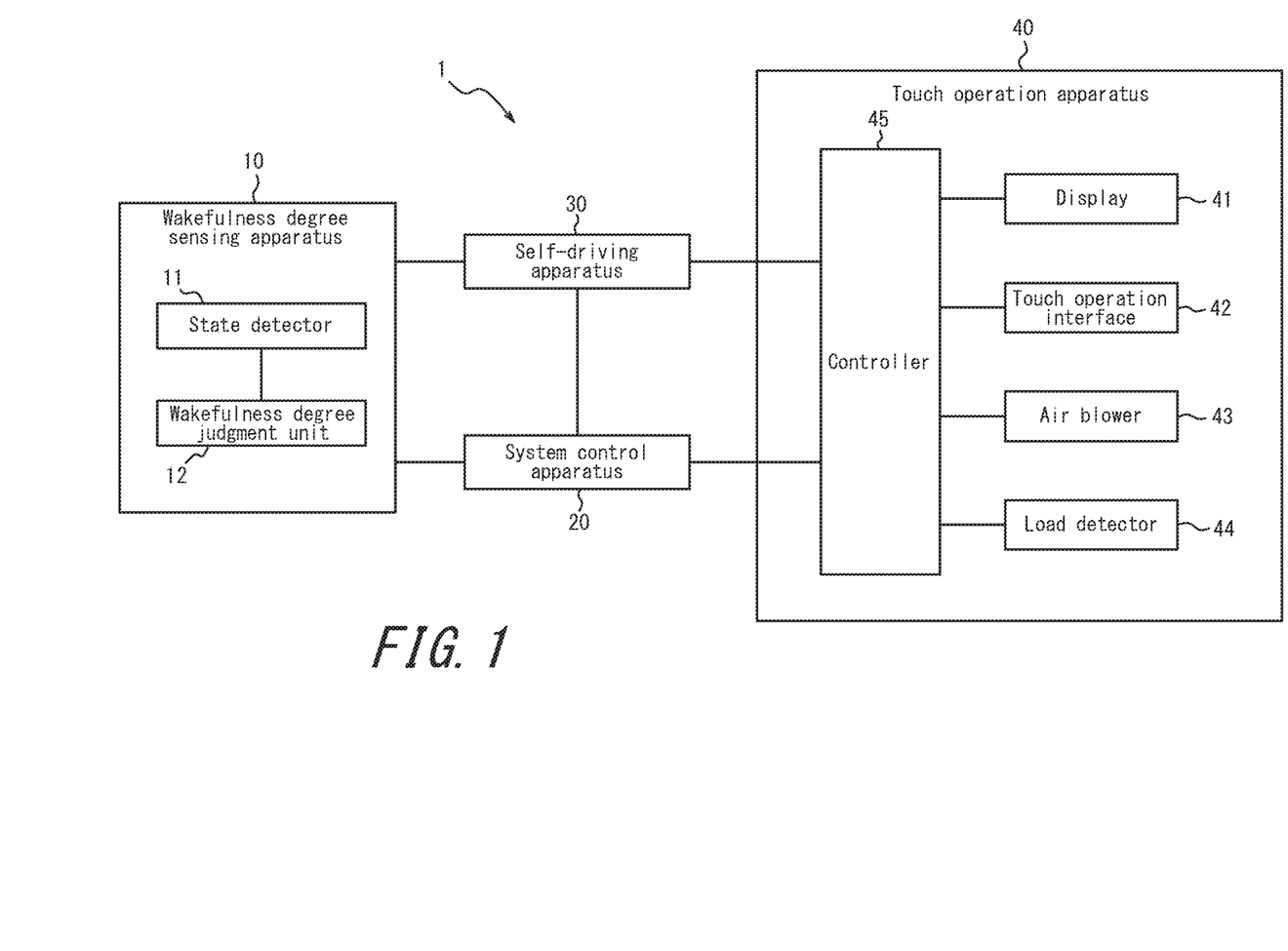
FIG. 1 is a functional block diagram illustrating the configuration of a wakefulness inducing system according to an embodiment of the present disclosure.

FIG. 1 is a functional block diagram illustrating the configuration of a wakefulness inducing system 1 according to an embodiment of the present disclosure. The wakefulness inducing system 1 includes a wakefulness degree sensing apparatus 10, a system control apparatus 20, a self-driving apparatus 30, and a touch operation apparatus 40. The wakefulness inducing system 1 senses a reduction in the degree of wakefulness of a driver during self-driving and induces a wakeful state in the driver.

The wakefulness degree sensing apparatus 10 includes a state detector 11 and a wakefulness degree judgment unit 12. The wakefulness degree sensing apparatus 10 senses the degree of wakefulness of the driver.

The state detector 11 is configured by a camera, an appropriate sensor such as a wearable sensor, and a control CAN or the like. The state detector 11 detects the state of the driver. For example, the state detector 11 detects the state of the driver such as the biological state, face orientation, gaze, blinking state, body movement, degree of excitement, degree of sentiment, enjoyment, satisfaction, emotions, desires, continuous driving (riding) time, visibility, glare, audibility, utterances, and the like of the driver. The biological information of the driver may include the brain waves, cerebral blood flow, blood pressure, blood glucose level, blood amino acids, HbA1c, γ-GPT, blood concentration of medications, heart rate, body temperature, apparent temperature, hunger, fatigue, and the like. The state detector 11 has been described as detecting the state of the driver, but this configuration is not limiting. The state detector 11 may also detect the state of a passenger.

The wakefulness degree judgment unit 12 acquires information related to the state of the driver detected by the state detector 11. The wakefulness degree judgment unit 12 estimates the degree of wakefulness of the driver based on the information related to the state of the driver acquired by the state detector 11. The wakefulness degree judgment unit 12 judges whether the estimated degree of wakefulness of the driver is equal to or less than a predetermined standard. The predetermined standard is, for example, a degree of wakefulness associated with the minimum necessary wakeful state of the driver in order for the driver to accurately monitor self-driving. When it is judged that the estimated degree of wakefulness of the driver is equal to or less than the predetermined standard, the wakefulness degree judgment unit 12 judges that the degree of wakefulness of the driver is low, which could impede monitoring of self-driving.

The wakefulness degree sensing apparatus 10 outputs information related to the sensed degree of wakefulness of the driver to the system control apparatus 20 and the self-driving apparatus 30.

The system control apparatus 20 is configured by a processor that controls and manages the entire wakefulness inducing system 1, starting with the functional blocks configuring the wakefulness inducing system 1. The system control apparatus 20 is configured by a processor such as a central processing unit (CPU) that executes programs with prescribed control procedures. Such programs are, for example, stored in a suitable storage apparatus.

The system control apparatus 20 controls the self-driving apparatus 30 and the touch operation apparatus 40 to appropriately induce a wakeful state in the driver based on the information related to the degree of wakefulness of the driver acquired by the wakefulness degree sensing apparatus 10. Specifically, upon acquiring information, from the wakefulness degree sensing apparatus 10, indicating that the degree of wakefulness of the driver estimated by the wakefulness degree judgment unit 12 is equal to or less than a predetermined standard, resulting in a low degree of wakefulness of the driver, the system control apparatus 20 controls the self-driving apparatus 30 and the touch operation apparatus 40 to induce a wakeful state in the driver.

The self-driving apparatus 30 is an apparatus including the necessary functions for controlling self-driving of a vehicle. For example, the self-driving apparatus 30 acquires vehicle-related information, such as information on the environment around the vehicle and the current position of the vehicle, with a suitable sensor. Based on the acquired vehicle-related information, the self-driving apparatus 30 automatically and appropriately controls vehicle-related states such as the vehicle speed, accelerator state, brake state, clutch state, gear state, windshield wiper state, audio state, warning state, light state, steering state, idle state, and air conditioner state.

The self-driving apparatus 30 may switch between manual driving and self-driving by receiving input from the driver. Each time a predetermined length of time elapses, the self-driving apparatus 30 provides an instruction to the driver indicating the need to perform some sort of action to judge whether the driver is appropriately monitoring self-driving.

Figure 2:
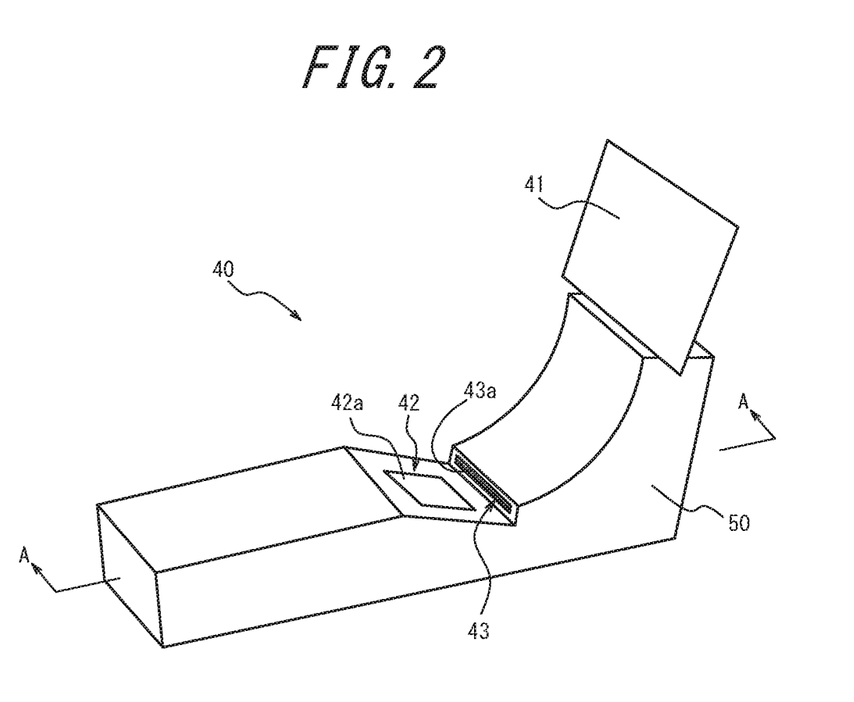
FIG. 2 is an external perspective view of the touch operation apparatus of FIG. 1.
Figure 3:
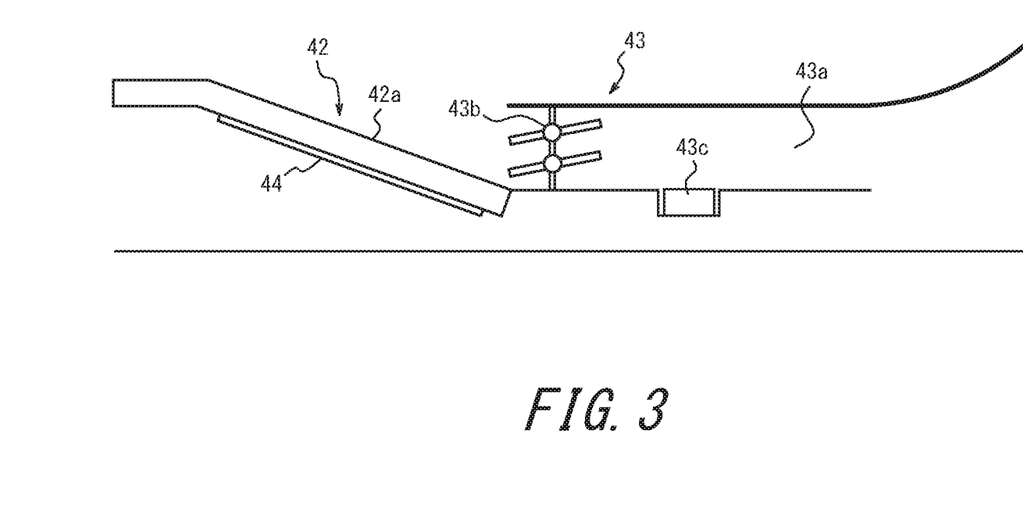
FIG. 3 is a cross-section along the A-A line, illustrating an enlargement of a portion of the touch operation apparatus of FIG. 2.

The touch operation apparatus 40 includes a display 41, a touch operation interface 42, an air blower 43, a load detector 44, and a controller 45. FIG. 2 is an external perspective view of the touch operation apparatus 40 of FIG. 1. FIG. 3 is a cross-section along the A-A line, illustrating an enlargement of a portion of the touch operation apparatus 40 of FIG. 2. Next, the configuration of the touch operation apparatus 40 is described with reference to FIG. 1 through FIG. 3.

The touch operation apparatus 40 accepts touch operation input by an operator on the touch operation interface 42. The operator can thereby perform a selection operation, an input operation, or the like on the touch operation interface 42 while viewing the separate display 41. The operator is, for example, the driver who is driving the vehicle or a passenger seated in the passenger seat.

The display 41 includes at least one screen. The display 41 may be configured by any display apparatus, such as a liquid crystal display. The display 41 is disposed in the instrument panel, for example, when configured by a liquid crystal display. The display apparatus configuring the display 41 may be a touch panel display or a display incapable of touch operations. The display 41 is described below as being a display incapable of touch operations.

The touch operation apparatus 40 may include a head-up display apparatus in addition to or instead of the display 41. In this case, the head-up display apparatus has a light emitter that emits display information as display light. The head-up display apparatus reflects the generated display light towards an observer, such as a driver, to display a virtual image beyond the front windshield. The observer is not limited to the driver and may, for example, be a passenger seated in the passenger seat.

The touch operation interface 42 is, for example, disposed in a center console 50. As illustrated in FIG. 2, the touch operation interface 42 is separate from the display 41. The touch operation interface 42 includes a touchpad 42a, as illustrated in FIG. 2 and FIG. 3. The operator places his arm on an armrest and his wrist on a palm rest, for example. In particular, the operator touches the touchpad 42a with a finger. The touch operation interface 42 detects contact by the operator's operating hand.

The touchpad 42a detects contact by a contacting object, such as the operator's finger or a stylus pen, at the corresponding contact position. By performing touch operations on the touch operation interface 42, in particular on the touchpad 42a, the operator operates information displayed on each screen configuring the display 41. The touchpad 42a is formed by transparent glass, for example, and can use a touch sensor configured by any system, such as a resistive film system, a capacitive system, a surface acoustic wave system, an infrared system, or an electromagnetic induction system. The touchpad 42a is described below as being a capacitive touchpad that uses a capacitive system.

The air blower 43 is installed on the center console 50 to be adjacent to the touch operation interface 42. The air blower 43 includes an air duct 43a, a vent 43b provided at the outlet of the air duct 43a, and a humidifier 43c disposed near the vent 43b. The air blower 43 blows warm or cool air towards the operation surface of the touch operation interface 42, i.e. the operation surface of the touchpad 42a. In other words, air passes through the air duct 43a and the vent 43b and is blown towards the operating surface of the touch operation interface 42 through the outlet. As the source of the air, the air blower 43 may use an air conditioner installed inside the car or use a dedicated, simple blower. The flow of air blowing from the outlet of the air blower 43 is adjusted by the controller 45 controlling the degree of opening of the vent 43b. In greater detail, the vent 43b of the air blower 43 is adjusted in the opening direction to increase the air flow. The vent 43b of the air blower 43 is adjusted in the closing direction to reduce the air flow. The air blower 43 can also blow air that includes water vapor by the controller 45 turning the humidifier 43c on or off.

The load detector 44 is disposed directly below the touch operation interface 42. The load detector 44 detects the vertical load on the touchpad 42a generated when the operator performs a swipe operation on the touch operation interface 42. At this time, the operator's finger used in the swipe operation experiences a vertical drag from the touchpad 42a as a reaction to the vertical load acting on the touchpad 42a. The load detector 44 outputs information related to the detected vertical load to the controller 45.

The controller 45 is a processor that controls and manages the touch operation apparatus 40 overall, starting with the functional blocks of the touch operation apparatus 40. The controller 45 is configured by a processor such as a central processing unit (CPU) that executes programs with prescribed control procedures. Such programs are, for example, stored in a suitable storage apparatus.

The control that the wakefulness inducing system 1 performs to induce a wakeful state in the driver is mainly described below. Specifically, the detailed explanation below focuses on the induction of a wakeful state in the driver by the system control apparatus 20 controlling the self-driving apparatus 30 and the touch operation apparatus 40 when the wakefulness degree sensing apparatus 10 senses a reduction in the degree of wakefulness of the driver.

When the wakefulness degree sensing apparatus 10 senses a reduction in the degree of wakefulness of the driver, the system control apparatus 20 controls the self-driving apparatus 30 to provide the driver with an instruction to move the operating hand of the driver to the touch operation interface 42. For example, the self-driving apparatus 30 uses the controller 45 to display the instruction on the display 41 and encourage the driver who recognizes the instruction to move his operating hand to the touch operation interface 42.

The instruction by the self-driving apparatus 30 may, for example, be related to a selection to be made by the driver with regard to self-driving. In greater detail, the self-driving apparatus 30 causes the driver to select whether to continue self-driving. For example, the self-driving apparatus 30 causes the message "Continue self-driving?" to be displayed on the display 41, and in this state, encourages the driver to provide touch operation input on the touch operation interface 42 to select "yes" or "no".

When the wakefulness degree sensing apparatus 10 senses a reduction in the degree of wakefulness of the driver, the self-driving apparatus 30 may acquire sensing information from the wakefulness degree sensing apparatus 10 and increase the frequency with which the driver is caused to select whether to continue self-driving.

The instruction by the self-driving apparatus 30 may, for example, be related to an operation performed by the driver on the touch operation interface 42 to operate in-vehicle audio visual equipment. In greater detail, the self-driving apparatus 30 may encourage the driver to operate the in-vehicle audio visual equipment. For example, the self-driving apparatus 30 performs control to switch in-vehicle audio equipment from off to on, to raise the volume of the in-vehicle audio equipment, to switch an in-vehicle monitor from off to on, to increase the brightness of the in-vehicle monitor, or the like. In this state, the self-driving apparatus 30 encourages the driver to return the in-vehicle audio visual equipment to its former state by touch operation input on the touch operation interface 42.

The self-driving apparatus 30 may provide the driver with one of the two instructions listed above as examples or provide the driver with two instructions simultaneously. The self-driving apparatus 30 may provide the driver with an instruction other than the aforementioned examples or may provide the driver with any instruction to move the operating hand of the driver to the touch operation interface 42.

Upon detection of contact by the operating hand of the driver on the touch operation interface 42 at the time the wakefulness degree sensing apparatus 10 has sensed a reduction in the degree of wakefulness of the driver, the system control apparatus 20 reduces the temperature of the operating hand on the touch operation interface 42. The operating hand of the driver who has a reduced degree of wakefulness is therefore suddenly cooled down, inducing a wakeful state in the driver. For example, the system control apparatus 20 may cool the touch operation interface 42 contacted by the operating hand of the driver, or the surrounding atmosphere, in advance. Upon detection of contact by the operating hand of the driver with the touch operation interface 42, the system control apparatus 20 may cool the touch operation interface 42 or the surrounding atmosphere.

In greater detail, the system control apparatus 20 may control the air blower 43 via the controller 45 for the air blower 43 to blow cool air, thereby reducing the temperature of the operating hand of the driver. Cool air refers to blown air that is at a lower temperature than the surrounding air temperature. The system control apparatus 20 may, for example, control the air blower 43 via the controller 45 so that the air blower 43 continually blows cool air towards the touch operation interface 42. The system control apparatus 20 may, for example, control the air blower 43 via the controller 45 so that the air blower 43 blows cool air towards the touch operation interface 42 when the wakefulness degree sensing apparatus 10 senses a reduction in the degree of wakefulness of the driver. The system control apparatus 20 may, for example, control the air blower 43 via the controller 45 so that the air blower 43 blows cool air towards the touch operation interface 42 when the touch operation interface 42 detects contact by the operating hand of the driver.

Upon detection of contact by the operating hand of the driver with the touch operation interface 42, the system control apparatus 20 may change the temperature of the operating hand by any method on the touch operation interface 42, even if the wakefulness degree sensing apparatus 10 has not sensed a reduction in the degree of wakefulness of the driver. For example, the system control apparatus 20 may reduce the temperature of the operating hand of the driver on the touch operation interface 42 in the same manner as described above. The sympathetic nerves of the driver consequently become dominant even if the driver is already in a wakeful state. A greater effect of wakefulness induction can thus be expected.

In greater detail, the system control apparatus 20 may control the air blower 43 via the controller 45 in the same manner as described above for the air blower 43 to blow cool air, thereby reducing the temperature of the operating hand of the driver.

The control of the air blower 43 by the system control apparatus 20 when the wakefulness degree sensing apparatus 10 does not sense a reduction in the degree of wakefulness of the driver is not limited to this example. For example, the system control apparatus 20 may increase the temperature of the operating hand of the driver on the touch operation interface 42. In greater detail, the system control apparatus 20 may control the air blower 43 via the controller 45 for the air blower 43 to blow warm air, thereby increasing the temperature of the operating hand of the driver. Warm air refers to blown air that is at a higher temperature than the surrounding air temperature.

The system control apparatus 20 may, for example, control the air blower 43 to switch to cool air or warm air each time contact by the operating hand of the driver is detected by the touch operation interface 42 when the wakefulness degree sensing apparatus 10 does not sense a reduction in the degree of wakefulness of the driver. The system control apparatus 20 may, for example, control the air blower 43 to alternate between cool air and warm air each time contact is detected. The system control apparatus 20 may, for example, control the air blower 43 to switch randomly between cool air and warm air each time contact is detected. This can prevent acclimation to a cool state, which could occur if the hand is continually cooled while the driver is in a wakeful state. The sensitivity of the driver's operating hand to temperature changes can thus be prevented from becoming dull. Consequently, the effect of inducing a wakeful state after a reduction in the degree of wakefulness of the driver is maintained.

The self-driving apparatus 30 has been described as providing the driver with the aforementioned instruction when the wakefulness degree sensing apparatus 10 senses a reduction in the degree of wakefulness of the driver, but this example is not limiting. Regardless of the degree of wakefulness of the driver, the self-driving apparatus 30 may provide the same instruction to the driver each time a predetermined length of time elapses as the original function to judge whether the driver is appropriately monitoring self-driving. The predetermined length of time may, for example, be a length of time prescribed by law or a length of time appropriately set by the vehicle manufacturer, the driver, and the like.

When the wakefulness degree sensing apparatus 10 has not sensed a reduction in the degree of wakefulness of the driver, the system control apparatus 20 may control the air blower 43 to switch to cool air or warm air with a similar method as above each time an instruction is provided to the driver after a predetermined length of time elapses.

Figure 4:
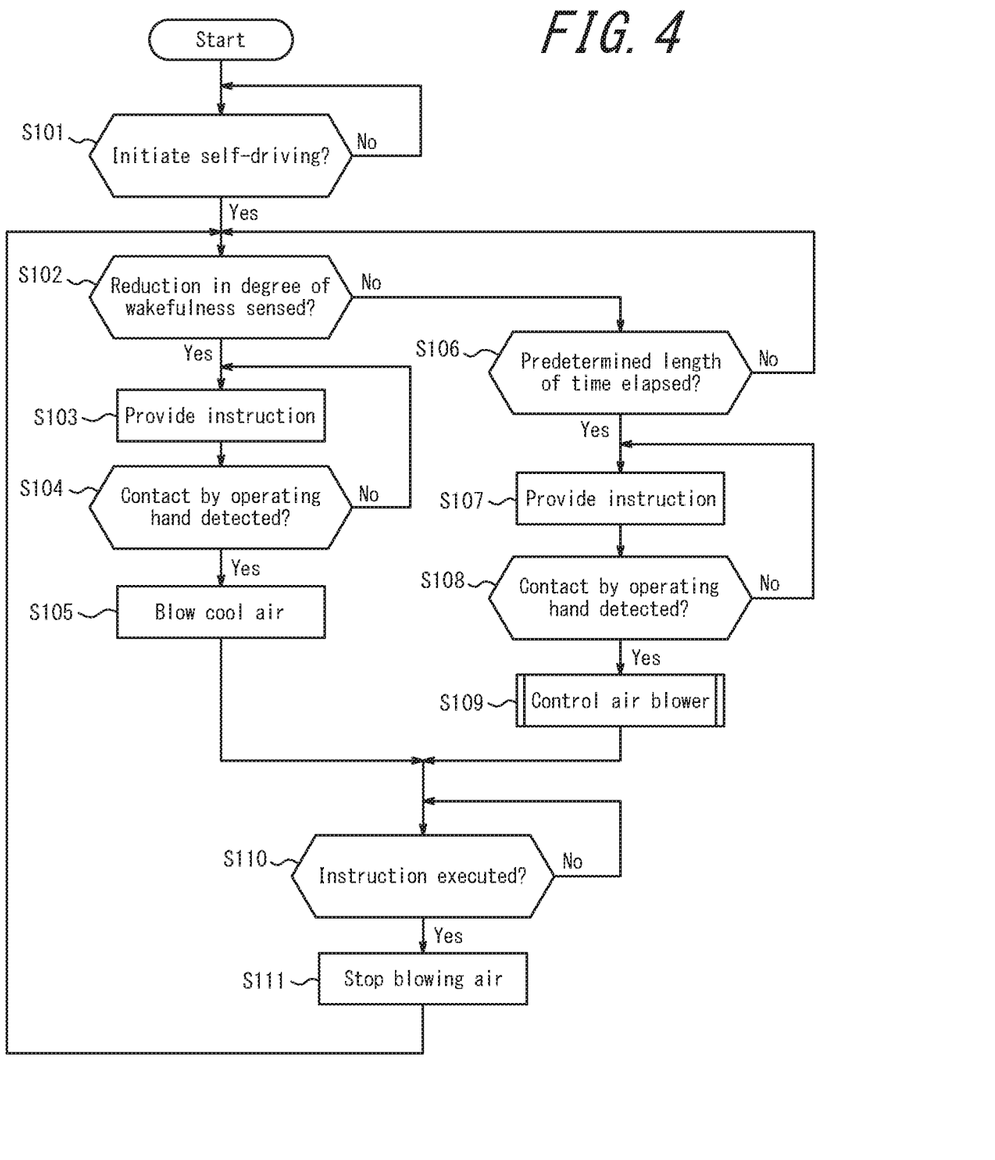
FIG. 4 is a flowchart illustrating an example of operations of the system control apparatus of FIG. 1.

FIG. 4 is a flowchart illustrating an example of operations of the system control apparatus 20 of FIG. 1.

The system control apparatus 20 judges whether self-driving has initiated (step S101). When judging that self-driving has initiated, the system control apparatus 20 proceeds to step S102. For example, the system control apparatus 20 causes the display 41 to display a self-driving initiation screen and requests that the driver make a selection. The system control apparatus 20 initiates self-driving using the self-driving apparatus 30 upon receiving touch operation input, on the touch operation interface 42, from the driver indicating to initiate self-driving. When judging that self-driving has not initiated, the system control apparatus 20 returns to step S101.

When judging that self-driving has initiated, the system control apparatus 20 judges whether a reduction in the degree of wakefulness of the driver has been sensed (step S102). The system control apparatus 20 judges whether the degree of wakefulness of the driver has reduced based on sensing information acquired from the wakefulness degree sensing apparatus 10. When judging that a reduction in the degree of wakefulness of the driver has been sensed, the system control apparatus 20 proceeds to step S103. When judging that a reduction in the degree of wakefulness of the driver has not been sensed, the system control apparatus 20 proceeds to step S106.

When judging that a reduction in the degree of wakefulness of the driver has been sensed, the system control apparatus 20 provides an instruction to the driver, via the self-driving apparatus 30, to move the operating hand of the driver to the touch operation interface 42 (step S103). The self-driving apparatus 30 causes the driver to select whether to continue self-driving based on touch operation input on the touch operation interface 42, for example. The self-driving apparatus 30 causes the driver to operate in-vehicle audio visual equipment based on touch operation input on the touch operation interface 42, for example.

The system control apparatus 20 judges whether contact by the operating hand of the driver has been detected by the touch operation interface 42 in response to the aforementioned instruction (step S104). When judging that contact by the operating hand of the driver has been detected, the system control apparatus 20 proceeds to step S105. When judging that contact by the operating hand of the driver has not been detected, the system control apparatus 20 returns to step S103 and provides the same instruction again.

In one example, the system control apparatus 20 controls the air blower 43 via the controller 45 to blow cool air when it is judged that contact by the operating hand of the driver has been detected (step S105). Subsequently, the system control apparatus 20 proceeds to step S110.

When judging that a reduction in the degree of wakefulness of the driver has not been sensed in step S102, the system control apparatus 20 judges whether a predetermined length of time has elapsed (step S106). When judging that the predetermined length of time has elapsed, the system control apparatus 20 proceeds to step S107. When judging that the predetermined length of time has not elapsed, the system control apparatus 20 returns to step S102 and repeats the same processing flow.

When judging that the predetermined length of time has elapsed, the system control apparatus 20 provides an instruction to the driver via the self-driving apparatus 30, as in step S103 (step S107).

The system control apparatus 20 judges whether contact by the operating hand of the driver has been detected by the touch operation interface 42 in response to the instruction provided in step S107 (step S108). When judging that contact by the operating hand of the driver has been detected, the system control apparatus 20 proceeds to step S109. When judging that contact by the operating hand of the driver has not been detected, the system control apparatus 20 returns to step S107 and provides the same instruction again.

In one example, the system control apparatus 20 controls the air blower 43 via the controller 45 to blow cool air or warm air when it is judged that contact by the operating hand of the driver has been detected (step S109).

The system control apparatus 20 judges whether the driver has executed the instruction provided in step S103 or step S107 (step S110). When judging that the driver has executed the instruction, the system control apparatus 20 proceeds to step S111. When judging that the driver has not executed the instruction, the system control apparatus 20 returns to step S110.

When judging that the driver has executed the instruction, the system control apparatus 20 controls the air blower 43 via the controller 45 to stop blowing air (step S111). Subsequently, the system control apparatus 20 returns to step S102 and repeats the same processing flow.

Figure 5:
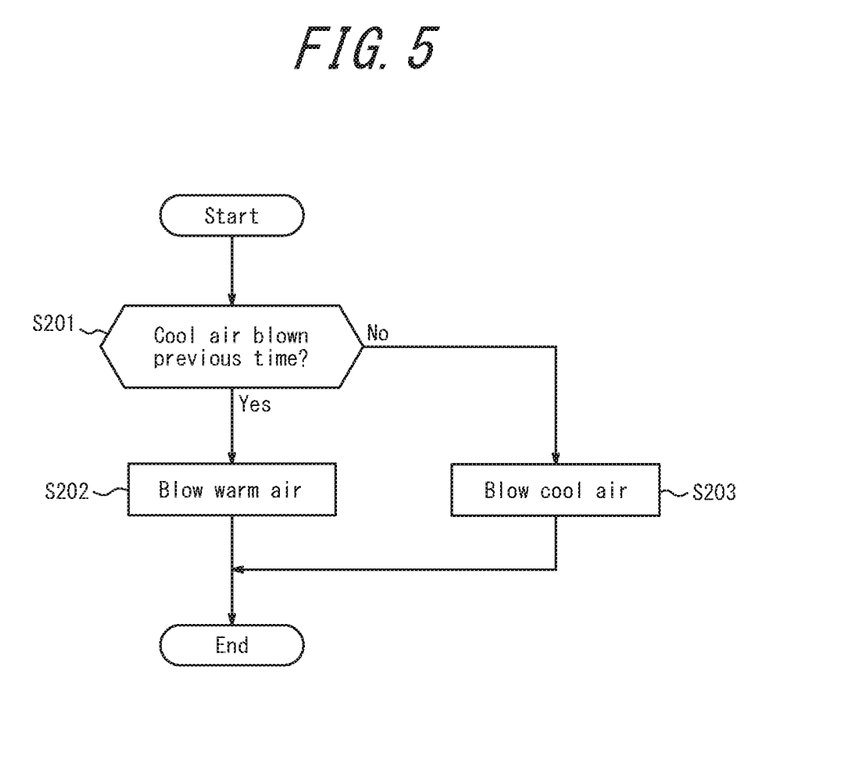
FIG. 5 is a flowchart illustrating an example of operations of the system control apparatus in step S109 of FIG. 4.

FIG. 5 is a flowchart illustrating an example of operations of the system control apparatus 20 in step S109 of FIG. 4. In greater detail, FIG. 5 is a flowchart illustrating an example of the system control apparatus 20 controlling the air blower 43 to alternate between cool air and warm air each time an instruction is provided to the driver after a predetermined length of time elapses. An example of the control of the air blower 43 by the system control apparatus 20, performed in step S109 of FIG. 4, is described in greater detail with reference to FIG. 5.

The system control apparatus 20 judges whether cool air has been blown by control of the air blower 43 based on the instruction of step S107 of FIG. 4, executed in the previous processing flow (step S201). When it is judged that cool air has been blown, the system control apparatus 20 proceeds to step S202. When it is judged that cool air has not been blown, i.e. that warm air has been blown, the system control apparatus 20 proceeds to step S203.

When it is judged that cool air has been blown, the system control apparatus 20 controls the air blower 43 to blow warm air (step S202).

When it is judged that warm air has been blown, the system control apparatus 20 controls the air blower 43 to blow cool air (step S203).

In this way, the wakefulness inducing system 1 is capable of appropriately inducing a wakeful state in a driver even in a self-driving vehicle. In other words, the wakefulness inducing system 1 can appropriately increase the degree of wakefulness of the driver. By lowering the temperature of the operating hand on the touch operation interface 42, the wakefulness inducing system 1 can appropriately induce a state of wakefulness in the driver even in a self-driving vehicle that does not require the steering wheel to be held. The wakefulness inducing system 1 can establish one location for cooling the operating hand of the driver by encouraging the driver to move the operating hand to the touch operation interface 42. In other words, the wakefulness inducing system 1 does not require an apparatus for detecting the position of the driver's operating hand that is to be cooled. The wakefulness inducing system 1 therefore allows a simplified configuration.

The wakefulness inducing system 1 can reliably cool the operating hand of the driver by cooling the touch operation interface 42 or the surrounding atmosphere in advance. The wakefulness inducing system 1 can thereby reliably induce a wakeful state in the driver to encourage the driver to appropriately monitor self-driving.

The wakefulness inducing system 1 can contribute to energy saving by cooling the touch operation interface 42 or the surrounding environment when contact by the operating hand of the driver is detected by the touch operation interface 42. The wakefulness inducing system 1 can suppress unnecessary energy consumption by cooling the touch operation interface 42 or the surrounding environment only when necessary.

The wakefulness inducing system 1 can cool the operating hand of the driver easily by using cool air blown by the air blower 43. The wakefulness inducing system 1 does not require a new cooling mechanism to increase the degree of wakefulness of the driver, since this purpose is served by the above-described air blower 43 provided in the touch operation apparatus 40 to improve the operability of the touchpad 42*a*. The wakefulness inducing system 1 thus allows a simplified configuration.

By providing an instruction related to a selection to be made by the driver with regard to self-driving, the wakefulness inducing system 1 can also use a portion of the functions unique to the self-driving apparatus 30 to increase the degree of wakefulness of the driver. Regardless of whether the degree of wakefulness of the driver has reduced, the self-driving apparatus 30 needs to judge whether the driver is appropriately monitoring self-driving each time a predetermined length of time elapses. The self-driving apparatus 30 therefore provides an instruction to the driver indicating the need to perform some sort of action. By sharing the functions of this self-driving apparatus 30, the wakefulness inducing system 1 does not require a new mechanism for increasing the degree of wakefulness of the driver. The wakefulness inducing system 1 thus allows a simplified configuration.

The wakefulness inducing system 1 allows continuous induction of the wakeful state in the driver by increasing the frequency of selection with the self-driving apparatus 30. When the frequency of selection with the self-driving apparatus 30 increases, the driver tends to place his operating hand continuously on the touch operation interface 42. The operating hand of the driver can therefore be cooled continuously while the operating hand is in contact with the touch operation interface 42. This allows the wakefulness inducing system 1 to maintain the wakeful state of the driver for an extended time.

By providing an instruction related to driver operation of in-vehicle audio visual equipment through the touch operation interface 42, the wakefulness inducing system 1 can encourage the driver to respond by a change in audio or video. The wakefulness inducing system 1 can more forcefully encourage the driver to take a predetermined action by thus appealing directly to the driver's sense of hearing or sight.

Although the present disclosure has been explained with reference to the drawings and examples, it is to be noted that various changes and modifications will be apparent to those of ordinary skill in the art based on the present disclosure. Therefore, such changes and modifications are to be understood as included within the scope of the present disclosure. For example, the functions and the like included in the various means and steps may be reordered in any logically consistent way. Means or steps may also be combined into one or divided.

The wakefulness inducing system 1 has been described as changing the temperature of the operating hand of the driver using cool air or warm air from the air blower 43 of the touch operation apparatus 40, but this configuration is not limiting. For example, the wakefulness inducing system 1 may include any temperature control element, such as a Peltier device, directly below the touchpad 42*a* in addition to or instead of the air blower 43. In this case, the wakefulness inducing system 1 may change the temperature of the operating hand of the driver by cooling or heating with the temperature control element, such as a Peltier device, in addition to or instead of cooling or heating with the air blower 43.

REFERENCE SIGNS LIST

1 Wakefulness inducing system
10 Wakefulness degree sensing apparatus
11 State detector
12 Wakefulness degree judgment unit
20 System control apparatus
30 Self-driving apparatus
40 Touch operation apparatus
41 Display
42 Touch operation interface
42*a* Touchpad
43 Air blower
43*a* Air duct
43*b* Vent
43*c* Humidifier
44 Load detector
45 Controller
50 Center console

The invention claimed is:
1. A wakefulness inducing system comprising:
   a wakefulness degree sensing apparatus configured to sense a degree of wakefulness of a driver;
   a touch operation apparatus comprising a touch operation interface on a center console configured to detect contact by an operating hand of the driver and an air blower disposed on the center console so as to be adjacent to the touch operation interface and configured to blow air; and
   a self-driving apparatus configured to control self-driving of a vehicle;
   wherein when judging that self-driving has initiated,
      the self-driving apparatus provides an instruction to the driver to move the operating hand to the touch operation interface on the center console, and
      a temperature of the operating hand is lowered by cool air blown by the air blower in the touch operation interface upon detection of contact of the operating hand by the touch operation interface.

2. The wakefulness inducing system of claim 1, wherein when judging that self-driving has initiated and the wakefulness degree sensing apparatus senses a reduction in the degree of wakefulness of the driver,
  the self-driving apparatus provides an instruction to the driver to move the operating hand to the touch operation interface on the center console, and
  a temperature of the operating hand is lowered by cool air blown by the air blower in the touch operation interface upon detection of contact of the operating hand by the touch operation interface.

3. The wakefulness inducing system of claim 1, wherein either the touch operation interface or a surrounding atmosphere thereof is cooled upon detection of contact of the operating hand by the touch operation interface.

4. The wakefulness inducing system of claim 1, wherein the instruction provided by the self-driving apparatus is related to a selection to be made by the driver with regard to self-driving.

5. The wakefulness inducing system of claim 4, wherein when the wakefulness degree sensing apparatus senses the reduction in the degree of wakefulness of the driver, a frequency of the instruction by the self-driving apparatus is increased.

6. The wakefulness inducing system of claim 1, wherein the instruction provided by the self-driving apparatus is related to operation of in-vehicle audio visual equipment operated by the driver on the touch operation interface.

7. The wakefulness inducing system of claim 1, wherein either the touch operation interface contacted by the operating hand or a surrounding atmosphere thereof is cooled in advance.

\* \* \* \* \*